US00PP16557P3

(12) United States Plant Patent

Miyazaki et al.

(10) Patent No.: US PP16,557 P3
(45) Date of Patent: May 16, 2006

(54) *VIOLA* PLANT NAMED 'SUNVIOBUHO'

(50) Latin Name: *Viola cornuta*
Varietal Denomination: Sunviobuho

(75) Inventors: Kiyoshi Miyazaki, Shiga (JP); Naoto Takamura, Shiga (JP)

(73) Assignee: Suntory Flowers Limited, Tokyo (JP)

( * ) Notice: Subject to any disclaimer, the term of this patent is extended or adjusted under 35 U.S.C. 154(b) by 41 days.

(21) Appl. No.: 10/949,334

(22) Filed: Sep. 27, 2004

(65) Prior Publication Data

US 2006/0070155 P1 Mar. 30, 2006

(51) Int. Cl.
*A01H 5/00* (2006.01)

(52) U.S. Cl. ..... Plt./323
(58) Field of Classification Search ..... Plt./323
See application file for complete search history.

(56) References Cited

PUBLICATIONS

"Flower & Green, Autumn and Winter Catalog 2003". Published by Suntory Flowers Limited of Tokyo, Japan, Jun. 1, 2003.
"Catalog for Commercial Breeders, Autumn '97 to Spring of '98", Published by Sakata Seed Co. of Japan, 1997.
"Catalog for Commercial Producers 1997–1998", Published by Taki Seed Co. of Japan, 1997.

*Primary Examiner*—Anne Marie Grunberg
*Assistant Examiner*—June Hwu
(74) *Attorney, Agent, or Firm*—Buchanan Ingersoll PC

(57) ABSTRACT

Disclosed herein is a new and distinct variety of *Viola cornuta,* named 'Sunviobuho', which is a vegetatively propagated variety. This new variety has a spreading growth habit with long prostrate stems. This *Viola* plant has many branches, and great profusion of blooms with the entire plant remaining in bloom for a considerable period of time. It displays dense green foliage, and single, small-sized flowers on long peduncles that are violet-blue and white in coloration. The plant exhibits good resistance to cold, diseases and pests.

2 Drawing Sheets

Botanical/commercial classification: *Viola cornuta/Viola* Plant.
Varietal denomination: cv. Sunviobuho.

BACKGROUND OF THE VARIETY

The present invention relates to a new and distinct variety of *Viola cornuta* named 'Sunviobuho' that originated from the crossing a *Viola* hybrid variety named '0V-41-9' as the female parent and '0V-80' as the male parent.

During April 2000, crossing of '0V-41-9' as the female parent and '0V-80' as the pollen parent was conducted at Yokaichi-shi, Shiga, Japan. In May 2000, some seeds were obtained from that crossing. In August 2000, the seeds were sown and 20 seedlings were obtained. Three of the seeding were selected in view of their spreading growth habit, small flower size and blue and white petal color. These seedlings were propagated by the use of cuttings and grown in pots, and then a plant trial was carried out beginning in October 2001, at Yokaichi-shi, Shiga, Japan. The botanical characteristics of that plant were then examined, using the similar varieties, 'Violetto Nive' and 'Alpine Summer', for comparison. As a result, one seedling was selected and it was concluded that this *Viola* plant is distinguishable from any other variety, whose existence is known to us, and is uniform and stable in its characteristics. The new variety of *Viola* plant was named 'Sunviobuho'.

The female parent '0V-41-9' (not patented in the U.S.) is our breeding line grown at Yokaichi-shi, Shiga, Japan, having a spreading growth habit with prostrate stems. It has smaller-sized flowers than the new variety 'Sunviobuho' and bi-colored flowers that are yellow and white in coloration.

The pollen parent '0V-80' (not patented in the U.S.) is our breeding line grown at Yokaichi-shi, Shiga, Japan, having a spreading growth habit with prostrate stems. It also has smaller-sized flowers than the new variety 'Sunviobuho', and the petals have a light blue coloration.

In the following description, the color information is in accordance with The R.H.S. Colour Chart of The Royal Horticultural Society, London, England.

SUMMARY OF THE INVENTION

This new variety is unlike any *Viola cornuta* commercially available as evidenced by the following unique combinations of characteristics.

1. Spreading growth habit having long prostrate stems and many branches.
2. Great profusion of blooms, with the entire plant remaining in bloom for a considerable period of time.
3. Single, small-sized flowers having violet-blue and white multi-colored petals that are borne on the long peduncles.

The new variety 'Sunviobuho' differs from the similar variety 'Violetto Nive' (not patented in the U.S.) in the following respects.

1. The peduncle length of 'Sunviobuho' is longer than that of 'Violetto Nive'.
2. The flowers of 'Sunviobuho' are smaller than those of 'Violetto Nive'.
3. The flowers of 'Sunviobuho' and 'Violetto Nive' differ in petal coloration. 'Sunviobuho' is bi-colored, the upper petal is violet-blue, and the lateral and lower petals are white. The flowers of 'Violetto Nive' are white.

4. Flowering time of 'Sunviobuho' is earlier than that of 'Violetto Nive'.

The new variety 'Sunviobuho' differs from the similar variety 'Alpine Summer' (not patented in the U.S.) in the following respects.

1. The peduncle length of 'Sunviobuho' is longer than that of 'Alpine Summer'.
2. The flowers of 'Sunviobuho' are larger than those of 'Alpine Summer'.
3. The flowers of 'Sunviobuho' and 'Violetto Nive' differ in petal coloration. 'Sunviobuho' is bi-colored, the upper petal is violet-blue, and the lateral and lower petals are white. The flowers of 'Alpine Summer' are bi-colored, the upper petal is violet, and lateral and lower petals are yellow with dark purple veins.
4. Flowering time of 'Sunviobuho' is earlier than that of 'Alpine Summer'.

The new variety of *Viola* plant 'Sunviobuho' was asexually reproduced by the use of cuttings at Yokaichi-shi, Shiga, Japan, and the homogeneity and stability thereof were confirmed.

The instant plant retains its distinctive characteristics and reproduces true to type in successive generations.

BRIEF DESCRIPTION OF THE PHOTOGRAPHS

The accompanying photographs show, as nearly true as it is reasonably possible to make the same in color illustrations of this character, typical specimens of the new cultivar. The plants had been reproduced by the use of cuttings and were photographed during May 2002 while growing outdoors in 24 cm pots at an age of approximately 7 months at Yokaichi-shi, Shiga, Japan.

DETAILED DESCRIPTION OF THE NEW VARIETY

Figure 1:
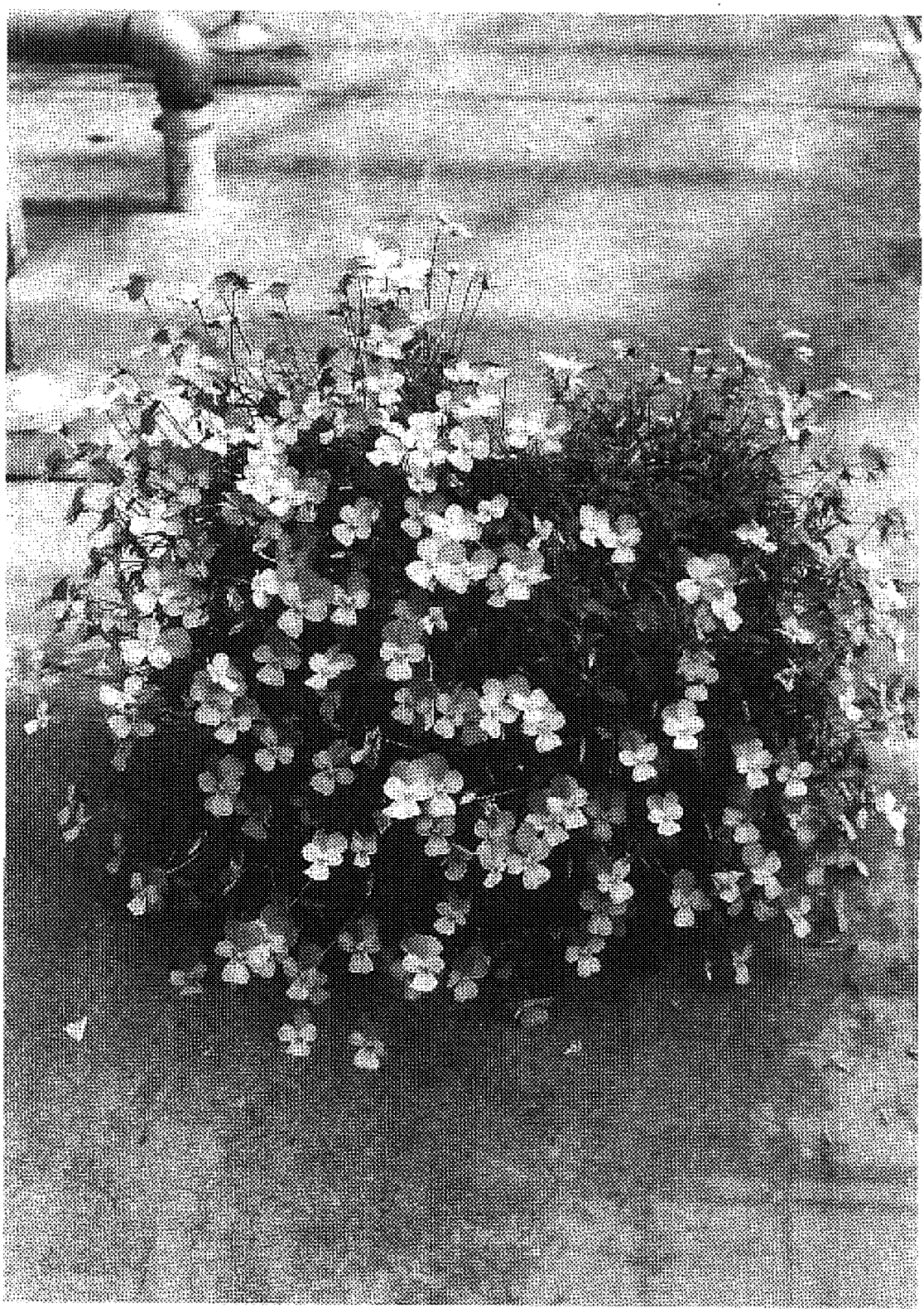
FIG. 1 illustrates an entire plant of the new variety while growing in a pot.
Figure 2:
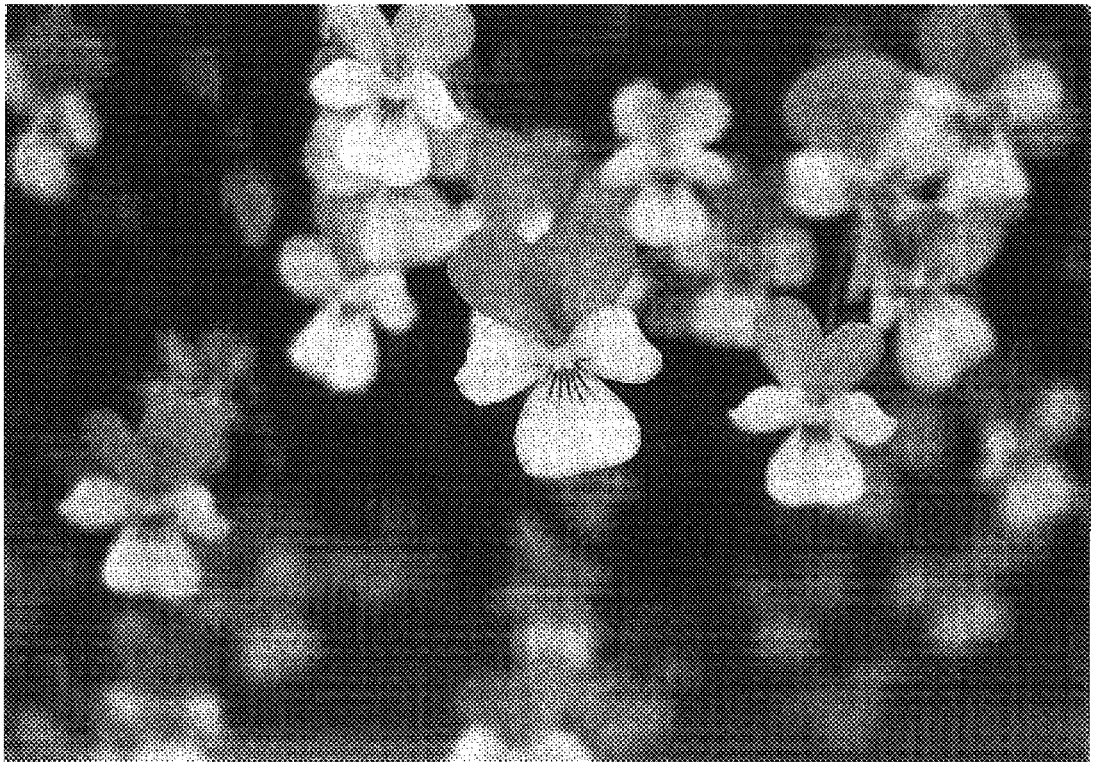
FIG. 2 illustrates a close view of the blossoms of the new variety.

The botanical characteristics of the new and distinct variety of *Viola cornuta* named 'Sunviobuho' are set forth below. The plants were observed during May 2002 at Yokaichi-shi, Shiga, Japan, at an age of approximately 7 months.

Plant:

*Stemmed or stemless.*—Stemmed.
*Growth habit.*—Spreading.
*Height.*—Approximately 14 cm.
*Spreading Area.*—Approximately 60 cm.

Stem:

*Length.*—Approximately 38 cm.
*Color.*—R.H.S.144B (Green group).
*Branches.*—Many.
*Pubescence.*—Present.
*Internode length.*—Approximately 1.5 cm.

Leaf:

*Phyllotaxis.*—Alternate.
*Overall shape.*—Lanceolate.
*Apex shape.*—Obtuse.
*Base shape.*—Obtuse.
*Margin.*—Crenate.
*Length.*—Approximately 3.0 cm.
*Width.*—Approximately 1.4 cm.
*Color of upper surface.*—R.H.S.137A (Green group).
*Color of under surface.*—R.H.S.137C (Green group).
*Leaf texture.*—Matte and smooth.
*Venation.*—Reticulate venation, not apparent except center venation.
*Petiole length.*—Approximately 2.7 cm.
*Petiole diameter.*—Approximately 0.5 mm.
*Petiole color.*—R.H.S. 144B (Yellow-green group).
*Stipule.*—Approximately 2.5 cm in length, 1.3 cm in width. Pinnately parted. Shape is narrowly ovate. Color of upper surface — R.H.S.137A (Green group). Color of under surface — R.H.S.137C (Green group).

Flower:

*Inflorescence.*—Flower solitary, axillary.
*Flower form.*—Single, 5 petals, 2 upper petals, 2 lateral petals and a spurred lower petal.
*Longitudinal diameter.*—Approximately 3.3 cm.
*Horizontal diameter.*—Approximately 2.5 cm.
*Petal margin.*—Entire, flat.
*Flower color.*—Multi-colored. Upper petal: R.H.S.91A (Violet-blue group). Lateral petal: R.H.S.155A (White group) with stripes near the throat R.H.S. 92B (Violet-blue group). Lower petal: R.H.S.155A (White group) with stripes near the throat R.H.S. 92B (Violet-blue group).
*Petal size.*—(Length×width). Upper petal: Approximately 1.8 cm×1.4 cm. Lateral petal: Approximately 1.2 cm×0.8 cm. Lower petal: Approximately 1.3 cm×1.5 cm.
*Petal shape.*—Upper petal: Rounded. Lateral petal: Elliptical. Lower petal: Cordate, spurred.
*Eye color.*—R.H.S.17B (Yellow-orange group) on the lower petal.
*Eye size.*—Length: Approximately 2.2 mm. Width: Approximately 2.4 mm.
*Spur length.*—Approximately 4.5 mm.
*Spur diameter.*—Approximately 1.0 mm.
*Spur color.*—R.H.S.116B (Blue-green group).
*Sepal.*—5 sepals, unequal, approximately 0.6 cm–1.2 cm, extended into short appendage.
*Sepal color.*—R.H.S. (44A (Yellow-green group) on both surfaces.
*Number of flowers.*—November to March; Approximately 20 flowers per a plant. March to June: Approximately 100–120 flowers per a plant.
*Peduncle length.*—Approximately 14.5 cm.
*Peduncle thickness.*—Approximately 0.8 mm.
*Peduncle color.*—R.H.S.137C (Green group).

Reproductive organs:

*Stamen*—Five stamens joined around the ovary. Two lower stamens are spurred.
*Stamen length.*—Approximately 2.0 mm.
*Anther color.*—R.H.S. 9D (Yellow group). Tip: R.H.S. 166C (Greyed-orange group).
*Pollen color.*—R.H.S. 9D (Yellow group).
*Pistil length.*—Approximately 4.5 mm.
*Stigma shape.*—Ellipsoidal.
*Stigma length.*—Approximately 1.0 mm.
*Stigma color.*—R.H.S. 144B (Yellow-green group).
*Style length.*—Approximately 1.0 mm.
*Style color.*—R.H.S. 144D (Yellow-green group).
*Ovary color.*—R.H.S. 144C (Yellow-green group).

Seeds:

*Seed.*—Some seed development has been observed.

*Seeds color.*—R.H.S. 165A (Greyed-orange group).

*Size.*—Approximately 2.0 mm in length, 1.0 mm in width.

Physical characteristics:

*Blooming period.*—Early November to June in Japan, except Hokkaido. A bloom commonly lasts approximately 5–7 days on the plant.

*Fragrance.*—Absent.

*Rain tolerance.*—Medium.

This variety has survived temperatures of at least −7° C. The plant grows well at temperature up to 25° C.

The lower and upper temperatures for the plant survival have not been evaluated in detail.

No serious damage by white fly, aphids, and by fungus and bacterial diseases has been observed.

This new variety of *Viola cornuta* plant 'Sunviobuho' is most suitable for potting, and growing in hanging baskets and in flower beds.

It is claimed:

1. A new and distinct variety of *Viola cornuta* plant named 'Sunviobuho', substantially as herein illustrated and described.

* * * * *